(12) United States Patent
Hall et al.

(10) Patent No.: US 9,846,109 B2
(45) Date of Patent: Dec. 19, 2017

(54) FLUID SAMPLING

(71) Applicant: SGS North America Inc., Rutherford, NJ (US)

(72) Inventors: Jim Hall, Pasadena, TX (US); Sven Lataire, Zevergem (BE)

(73) Assignee: SGS North America Inc., Rutherford, NJ (US)

(*) Notice: Subject to any disclaimer, the term of this patent is extended or adjusted under 35 U.S.C. 154(b) by 61 days.

(21) Appl. No.: 14/923,997

(22) Filed: Oct. 27, 2015

(65) Prior Publication Data

US 2017/0115190 A1 Apr. 27, 2017

(51) Int. Cl.
| | |
|---|---|
| *G01N 1/22* | (2006.01) |
| *G01N 1/20* | (2006.01) |
| *B08B 5/02* | (2006.01) |
| *F17C 7/00* | (2006.01) |
| *G01N 1/14* | (2006.01) |
| *G01N 1/10* | (2006.01) |

(52) U.S. Cl.
CPC .......... *G01N 1/2247* (2013.01); *B08B 5/02* (2013.01); *F17C 7/00* (2013.01); *G01N 1/2035* (2013.01); *G01N 1/2226* (2013.01); *G01N 2001/105* (2013.01); *G01N 2001/1427* (2013.01); *G01N 2001/2064* (2013.01); *G01N 2001/2238* (2013.01); *Y10T 137/4259* (2015.04)

(58) Field of Classification Search
CPC ......... G01N 2001/1427; G01N 1/2035; G01N 2001/2064; Y10T 137/4259
USPC .............................................. 73/863–864.91
See application file for complete search history.

(56) References Cited

U.S. PATENT DOCUMENTS

| | | | |
|---|---|---|---|
| 2,637,211 A | * | 5/1953 | Norman, Jr. ............. G01N 1/14 73/864.34 |
| 4,712,434 A | | 12/1987 | Herwig et al. |
| | | | (Continued) |

FOREIGN PATENT DOCUMENTS

| | | |
|---|---|---|
| DE | 3822564 A1 | 10/1989 |
| DE | 199414878 A1 | 2/1995 |
| DE | 29500412 A1 | 4/1995 |

OTHER PUBLICATIONS

International Search Report and Written Opinion of the International Searching Authority dated Feb. 21, 2017, in International Application No. PCT/US2016/059015; 12 pages.

*Primary Examiner* — Kevin Murphy
(74) *Attorney, Agent, or Firm* — Fish & Richardson P.C.

(57) ABSTRACT

A fluid sampling device having a first conduit configured to couple an outlet of a fluid source to a sample inlet port; a second conduit configured to couple a sample outlet port to an inlet of the fluid source; an expansion chamber including an inlet and an outlet coupled to the first and second conduits by a valve assembly; and a pressure relief valve configured to couple the outlet of the expansion chamber to the inlet of the fluid source. The fluid sampling device facilitates acquisition of a fluid sample and subsequent purging of its internal components while inhibiting the release of sample fluid to the surrounding environment, thereby protecting the environment and sampling personnel from harmful chemical release. The fluid sampling device may facilitate a sample acquisition process that provides closed-loop flush and expansion operations for obtaining a representative sample at the appropriate fill density of the sample vessel.

21 Claims, 5 Drawing Sheets

(56) References Cited

U.S. PATENT DOCUMENTS

| | | | |
|---|---|---|---|
| 4,800,761 A | | 1/1989 | Spencer |
| 4,974,456 A | * | 12/1990 | Ortiz .................. G01N 1/10 |
| | | | 141/59 |
| 4,987,785 A | | 1/1991 | Spencer |
| 5,116,330 A | | 5/1992 | Spencer |
| 5,131,282 A | | 7/1992 | Kuhner |
| 5,251,495 A | | 10/1993 | Kuhner |
| 5,370,005 A | | 12/1994 | Fjerdingstad |
| 5,370,146 A | * | 12/1994 | King .................... F17D 3/10 |
| | | | 134/166 C |
| 5,600,075 A | | 2/1997 | Peterson |
| 7,647,846 B2 | | 1/2010 | Coleman et al. |
| 7,921,739 B2 | | 4/2011 | Fjerdingstad et al. |
| 2012/0315163 A1 | * | 12/2012 | Yan ..................... F04B 19/20 |
| | | | 417/375 |
| 2013/0192339 A1 | * | 8/2013 | Kriel .................... G01N 1/22 |
| | | | 73/23.36 |
| 2014/0230521 A1 | | 8/2014 | Thompson |

* cited by examiner

FLUID SAMPLING

TECHNICAL FIELD

This specification generally relates to systems, devices, and methods for acquiring a fluid sample.

BACKGROUND

Fluid sampling devices are used in many industries to acquire a measured volume of fluid from an independent fluid source for transport to a remote testing location. Testing of the fluid sample may include detecting the presence of contaminants and/or determining the fluid's physical properties and composition. Generally, the fluid from the fluid source is circulated through the fluid sampling device, which facilitates the capture of a representative sample in a sample vessel that is detachable from the sampling device.

SUMMARY

This specification describes technologies related to systems, apparatus, and methods for acquiring a fluid sample.

In one aspect of the present disclosure, a fluid sampling device includes: a first conduit configured to couple an outlet of a fluid source to a sample inlet port; a second conduit configured to couple a sample outlet port to an inlet of the fluid source; an expansion chamber including an inlet and an outlet coupled to the first and second conduits by a valve assembly; and a pressure relief valve configured to couple the outlet of the expansion chamber to the inlet of the fluid source. The first conduit is further configured to be coupled to an inert gas source, such that: inert gas from the inert gas source pushes fluid within the first and second conduits toward the inlet of the fluid source when the valve assembly is in a first position, thereby purging the first and second conduits, and inert gas from the inert gas source pushes fluid within the expansion chamber towards the inlet of the fluid source when the valve assembly is in a second position and the pressure relief valve is opened, thereby purging the expansion chamber.

In some embodiments, the fluid includes a liquefied gas.

In some embodiments, the inert gas includes at least one of carbon dioxide, molecular oxygen, and molecular nitrogen.

In some embodiments, the fluid sampling device further includes a portable housing supporting the first and second conduits, the expansion chamber and the pressure relief valve.

In some embodiments, the sample inlet port and the sample outlet port include quick connect fittings.

In some embodiments, the valve assembly includes a tandem valve including a pair of three-way valves, a first of the three-way valves coupling the inlet of the expansion chamber to the second conduit, and a second of the three-way valves coupling the outlet of the expansion chamber to first conduit.

In some embodiments, the fluid sampling device further includes a booster pump configured to be coupled to the first conduit, and operation of the booster pump induces fluid from the outlet of the fluid source to flow through the first conduit towards the sample inlet port. In some embodiments, the booster pump includes a gas drive, and an intake port of the gas drive is configured to be coupled to the inert gas source. In some embodiments, the fluid sampling device further includes an inert-gas routing valve configured to modulate coupling of the inert gas source between the first conduit and the intake port of the gas drive of the booster pump. In some embodiments, the fluid sampling device further includes a booster-pump valve configured to modulate coupling of the first conduit with a high-pressure outlet of the booster pump.

In another aspect of the present disclosure, a fluid sampling device includes: a first conduit configured to couple an outlet of a fluid source to a sample inlet port; a second conduit configured to couple a sample outlet port to an inlet of the fluid source; an expansion chamber including an inlet and an outlet coupled to the first and second conduits by a valve assembly; a booster pump configured to be coupled to the first conduit, such that operation of the booster pump induces fluid from the outlet of the fluid source to flow through the first conduit towards the sample inlet port; and a portable housing supporting the first and second conduits, the expansion chamber and the booster pump.

In some embodiments, the fluid sampling device further includes a sample vessel coupled to the sample inlet port and the sample outlet port. In some embodiments, fluid from the fluid source flows in a closed loop between the sample vessel and the fluid source when the valve assembly is in a first position, thereby flushing the sample vessel, and the fluid flows in a closed loop between the sample vessel and the expansion chamber when the valve assembly is in a second position, thereby expanding a portion of the fluid in the sample vessel.

In some embodiments, the booster pump includes a gas drive, and an intake port of the gas drive is configured to be coupled to an inert gas source. In some embodiments, the fluid sampling device further includes an inert-gas routing valve configured to modulate coupling of the inert gas source between the first conduit and the intake port of the gas drive of the booster pump.

In some embodiments, the fluid sampling device further includes a booster-pump valve configured to modulate coupling of the first conduit with a high-pressure outlet of the booster pump.

In some embodiments, the valve assembly includes a tandem valve including a pair of three-way valves, a first of the three-way valves coupling the inlet of the expansion chamber to the second conduit, and a second of the three-way valves coupling the outlet of the expansion chamber to first conduit.

In yet another aspect of the present disclosure, a method of purging a fluid sampling device includes: coupling a fluid conduit of the fluid sampling device to an inert gas source; circulating the inert gas through the fluid conduit; circulating the inert gas through an expansion chamber of the fluid sampling device; and depositing at least a portion of the inert gas and at least a portion of any sample fluid purged from the fluid conduit and the expansion chamber directly from the fluid sampling device to a source of the sample fluid coupled to the fluid sampling device.

In some embodiments, the inert gas includes at least one of carbon dioxide, molecular oxygen, and molecular nitrogen.

In some embodiments, the method further includes circulating the inert gas through a valve assembly including a tandem valve including a pair of three-way valves, a first of the three-way valves coupling an inlet of the expansion chamber to the fluid conduit, and a second of the three-way valves coupling an outlet of the expansion chamber to the fluid conduit. In some embodiments, the method further includes modulating the valve assembly between first and second positions to cause discrete puffs of inert gas to circulate through the expansion chamber. In some embodiments, the method further includes engaging an override device of a pressure relief valve coupled to the outlet of the expansion chamber, thereby fluidically coupling the expansion chamber with the source of the sample fluid.

The details of one or more implementations of the subject matter described in this specification are set forth in the accompanying drawings and the description below. Other features, aspects, and advantages of the subject matter will become apparent from the description, the drawings, and the claims.

DETAILED DESCRIPTION

The present disclosure relates to systems, devices, and methods for acquiring a representative fluid sample from a fluid source. In some embodiments, a fluid sampling device is appropriately configured to facilitate the acquisition of a fluid sample and the subsequent purging of its internal components, while inhibiting the release of sample fluid to the surrounding environment. This protects the environment and sampling personnel from harmful chemical release. In some examples, the fluid sampling device may facilitate a sample acquisition process that provides closed-loop flush and expansion operations for obtaining a representative sample at the appropriate fill density of the sample vessel. In some examples, the fluid sampling device may facilitate an inert-gas purging process that deposits residual sample fluid from previous sampling operations directly back into the fluid source. In some embodiments, a fluid sampling device includes an internal booster pump operable to maintain the pressure of the sample fluid above its vapor pressure to inhibit inadvertent flashing of a two-phase sample fluid to a gas phase. Thus, the fluid sampling device can facilitate sample acquisition from an external fluid source without an independent pressure source (e.g., a tank or reservoir).

Figure 1:
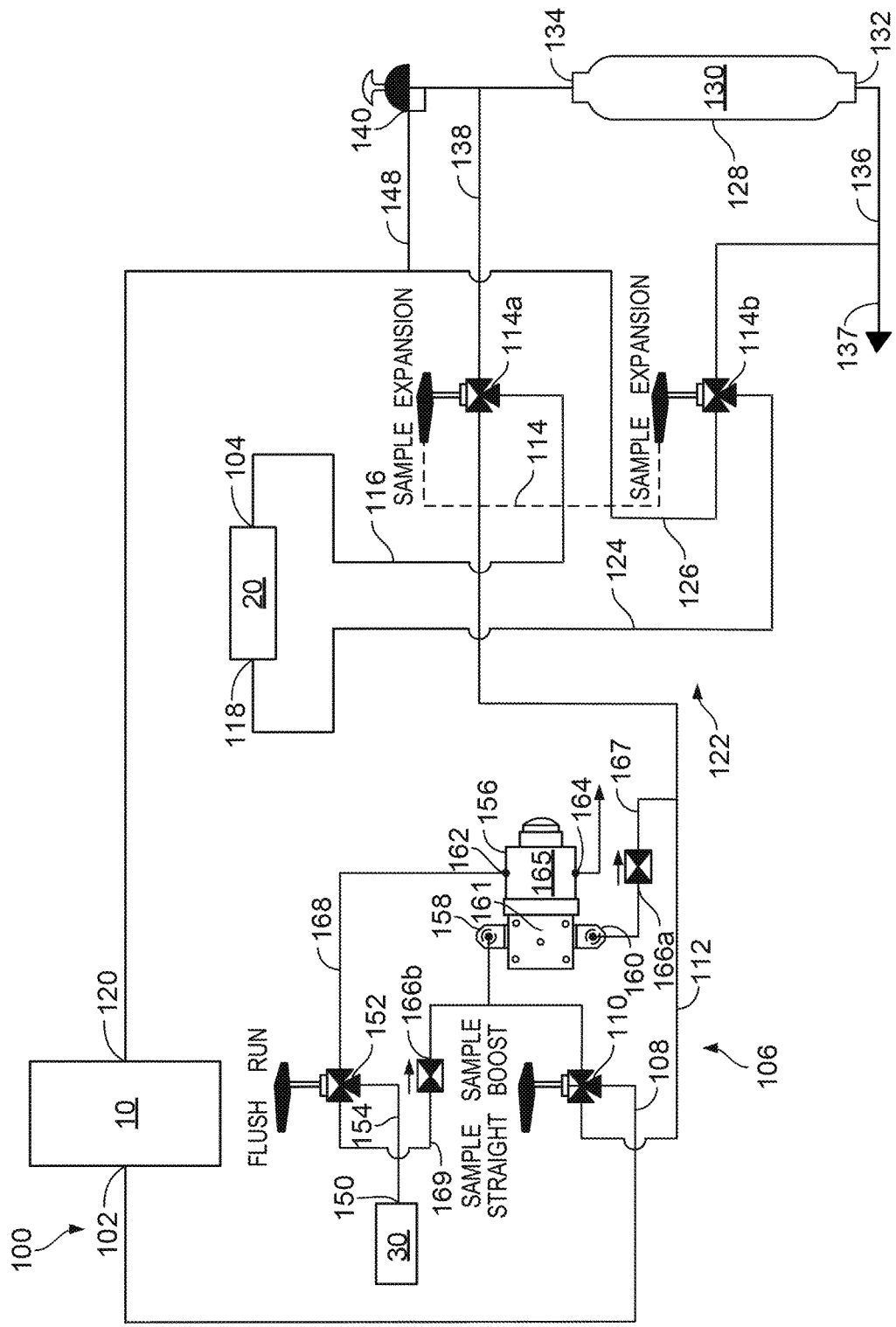
FIG. 1 is diagram of a fluid sampling device.

FIG. 1 is a diagram of an example fluid sampling device 100 in accordance with one or more embodiments of the present disclosure. In this example, the fluid sampling device 100 includes a fluid source outlet 102, a fluid source inlet 120, a sample inlet port 104, a sample outlet port 118, and an expansion chamber 128. As described below, the various components of the fluid sampling device 100 are coupled to one another fluidically by several segments of fluid conduit. The fluid conduit is suitable for conveying pressurized fluid (e.g., liquefied gas) throughout the fluid sampling device 100. Thus, the conduit may be designed or configured differently depending on the application of the sampling device 100. For example, in various applications of the sampling device 100, one or more of the conduit segments can be a substantially rigid or flexible conduit formed from a metallic or polymeric material. In various applications, the conduit segments are sized to achieve specified fluid flow characteristics (e.g., flow rate and pressure). In a particular example, one or more of the conduit segments include tubular conduit having a diameter of about ¼ inch.

In some embodiments, the fluid source outlet 102 and inlet 120 include couplings (e.g., quick connect couplings) suitable for connection with the mating hardware of an external fluid source 10 containing the to-be-sampled fluid. In some implementations, the fluid source 10 may include a chemical processing system for treating liquefied petroleum gas. Of course, various other implementations are contemplated within the scope of the present disclosure. In particular, various other types of fluids for sampling are contemplated (e.g., other types of liquefied hydrocarbon gas, such as liquefied natural gas and butadiene), as well as various other types of sampling platforms (e.g., production pipelines and storage tanks held in a stationary facility or in transit on a train, truck, ship or barge). In some embodiments, the sample inlet port 104 and outlet port 118 include couplings (e.g., quick connect couplings) suitable for connection with the mating hardware of a sample vessel 20 appropriately designed for retaining the acquired fluid sample. In some implementations, the sample vessel 20 may include a metallic, pressure-rated cylinder equipped with inlet and outlet isolation valves. Other appropriate sample vessel configurations are also within the scope of the present disclosure.

The fluid source outlet 102 is coupled to the sample inlet port 104 by a fluid conduit 106. In this example, the fluid conduit 106 includes a first conduit segment 108, a second conduit segment 112, and a third conduit segment 116. The conduit segment 108 leads from the fluid source outlet 102 to a booster-pump valve 110. The conduit segment 112 leads from the booster-pump valve 110 to an expansion valve 114a. The conduit segment 116 leads from the expansion valve 114a to the sample inlet port 104. The sample outlet port 118 is coupled to the fluid source inlet 120 by a fluid conduit 122. In this example, the fluid conduit 122 includes a first conduit segment 124 and a second conduit segment 126. The conduit segment 124 leads from the sample outlet port 118 to an expansion valve 114b. The conduit segment 126 leads from the expansion valve 114b to the fluid source inlet 120.

The expansion chamber 128 includes a main body 130, an inlet end 132 and an outlet end 134. The inlet end 132 is coupled to the expansion valve 114b, and therefore the fluid conduit 122, by a conduit segment 136. The outlet end 134 is coupled to the expansion valve 114a, and therefore the fluid conduit 106, by a conduit segment 138. Thus, during use, the expansion valves 114a and 114b provide a valve assembly 114 to govern the flow of fluid between the fluid source 10, sample vessel 20, and the expansion chamber 128. In this example, each of the expansion valves 114a and 114b includes a three-way valve. Further, in some implementations, the expansion valves 114a, 114b may be operatively coupled to one another (e.g., mechanically, electronically, and/or communicatively) such that they are adjustable in tandem.

The valve assembly 114 facilitates flow patterns for the sample fluid. In a first flow pattern, when adjusted to the "Sample" position, the expansion valves 114a and 114b inhibit or prevent flow to the expansion chamber 128, and allow the sample fluid to flow in a closed loop between the fluid source 10 and the sample vessel 20. More specifically, fluid flows from the fluid source outlet 102 to the sample inlet port 104 via the fluid conduit 106, and from the sample outlet port 118 to the fluid source inlet 120 via the fluid conduit 122. Thus, the sample vessel 20 can be continuously "flushed" with fluid for a period of time (between about 15 and 30 minutes) to remove potential contaminants from various components fluid sampling device 100, which may provide for a more representative sample. In a second flow pattern, when adjusted to the "Expansion" position, the expansion valves 114a and 114b inhibit or prevent flow to the fluid source 10, and allow the sample fluid to flow in a closed loop between the sample vessel 20 and the expansion chamber 128. More specifically, fluid flows from the sample outlet port 118 to the inlet end 132 of the expansion chamber 128, and from the expansion chamber's outlet end 134 to the sample inlet port 104. The expansion chamber 128 is maintained at a lower pressure than the sample vessel 20, and therefore creates a pressure differential that draws off a portion of the fluid contained in the sample vessel 20 as the pressure equalizes. In some implementations, the expansion chamber 128 is maintained at a vacuum pressure below the atmospheric level (e.g., such as between about −100 psig and about −150 psig). When the sample fluid is a compressed gas (e.g., liquefied petroleum or natural gas), exposure to the low pressure of the expansion chamber 128 causes a portion (e.g., about 20%) of the compressed liquid in the sample vessel 20 to expand to a gas, thereby reducing the fill density of the sample vessel 20. Thus, expansion chamber 128 can be appropriately configured to achieve a predetermined maximum fill density (e.g., about 80%) of the sample vessel 20.

A pressure relief valve 140 is coupled to the outlet end 134 of the expansion chamber 128, and a conduit segment 148 leads from the pressure relief valve 140 to the fluid source inlet 120. The pressure relief valve 140 can be set to automatically open and evacuate fluid from the expansion chamber 128 and back to the fluid source 10 when a predetermined activation pressure (e.g., at least about 135 psig, such as about 150 psig) is reached. Further, as discussed below, the pressure relief valve 140 can also be operated via an override device (e.g., an override handle) to facilitate on-demand purging of sample fluid from the expansion chamber 128 with inert gas. In some examples, the override device is configured to open the pressure relief valve 140 without changing the predetermined activation pressure.

Still referring to FIG. 1, the fluid sampling device 100 further includes an inert gas inlet 150 and a gas routing valve 152. In some embodiments, the inert gas inlet 150 includes a coupling (e.g., a quick connect coupling) suitable for connection with the mating hardware of an inert gas source 30. In some implementations, the inert gas source 30 includes a pressurized vessel containing an inert gas. As used herein, an inert gas refers to a gas that does not react with the sample fluid, such as compressed air, carbon dioxide, nitrogen gas, and oxygen gas. Other appropriate configurations for providing the inert gas source 30 are also within the scope of the present disclosure. The inert gas inlet 150 is coupled to the gas routing valve 152 via a conduit segment 154. In this example, the gas routing valve 152 includes a three-way valve coupling the inert gas source 30 to a booster pump 156. In some embodiments, the booster pump 156 provides a boost ratio of between about 1.25 and about 10. In some embodiments, the booster pump 156 can boost the pressure of the sample fluid up to about 150 psig. The booster pump 156 is designed to facilitate the sampling process in various applications where the fluid source 10 does not provide sufficient pressure differential to drive the sample fluid through the sampling device 100 and/or where a liquefied sample fluid must be maintained above its vapor pressure to avoid flashing. Thus, the booster pump 156 facilitates operation of the fluid sampling device 100 in various environments that do not incorporate an independent pressure device, such as a storage tank in transport on a train, truck or barge.

The booster pump 156 includes a suction port 158, a discharge port 160, an intake port 162 and an exhaust port 164. The suction port 158 and the discharge port 160 are coupled to the pump portion 161 of the booster pump 156; and the intake port 162 and the exhaust port 164 are coupled to the drive portion 165 of the booster pump 156 that drives the pump portion 161. In some examples, the pump portion 161 may include a piston- or plunger-type device designed to boost the pressure of the sample fluid when driven by the drive portion 165. Thus, during a sampling procedure, the booster pump 156 is designed to receive relatively low pressure fluid from the sample source at the suction port 158 and expel the fluid at a higher pressure via the discharge port 160. In this example, the drive portion 165 is propelled by pressurized gas from the inert gas source 30. The inert gas enters the booster pump's pneumatic drive portion 165 via the intake port 162 and is ejected from the pump 156 through the exhaust port 164 once the stored energy has been converted to mechanical work operating the pump portion 161. A check valve 166a is provided directly downstream of the discharge port 160 on a conduit segment 167 to inhibit or prevent fluid backflow through the booster pump 156. As shown, the conduit segment 167 intersects with the fluid conduit 106 that leads the sample fluid to the expansion valve 114a. When the booster-pump valve 110 (a three-way valve in this example) is adjusted to the "Sample Boost" position, fluid from the fluid source 10 is routed via conduit segment to the suction port 158 of the booster pump 156 to be pressurized. Conversely, when the booster-pump valve 110 is adjusted to the "Sample Straight" position, the sample fluid is blocked from the suction port 158 and routed directly to the expansion valve 114a via the conduit segment 112, bypassing the booster pump 156. As suggested above, the "Sample Straight" position may be used when the fluid sampling device 100 is installed for use with a fluid source 10 that provides sufficient pressure to the sample fluid.

As described above, the inert gas can be used to drive the booster pump 156. Additionally, the inert gas can be used to purge the sampling device 100 of residual fluid from previous sampling operations. When the gas routing valve 152 is adjusted to the "Run" position, inert gas is routed to the intake port 162 of the booster pump 156 via a conduit segment 168, and the sampling operations may proceed as described above. In some embodiments, the gas routing valve 152 can also be adjusted to an "Off" position (not shown) when the booster pump 156 is not in use. However, when the gas routing valve 152 is adjusted to the "Purge" position, inert gas is blocked from the intake port 162 and alternatively routed to a conduit segment 169 fitted with a check valve 166b to inhibit or prevent backflow. If the booster-pump valve 110 is adjusted to the "Sample Straight" position, inert gas enters the suction port 158 of the booster pump 156 and purges the pump portion 161. If the booster-pump valve 110 is adjusted to the "Sample Boost" position, at least a portion of the inert gas is pushed back through the booster-pump valve 110 to purge the fluid source outlet 102.

Inert gas passing through the booster pump 156 enters the fluid conduit 106 that leads to the expansion valve 114a. When the expansion valves 114a and 114b are adjusted to the "Sample" position, the inert gas is routed through the segments of fluid conduit 106 and 122 to purge the sample inlet port 104 and the sample outlet port 118. The inert gas and any purged fluid then exits the sampling device 100 through the fluid source inlet 120. In some embodiments, the sample vessel 20 is replaced by a conduit segment (not shown) to maintain fluid flow between the sample inlet port 104 and outlet port 118 during the purging process. When the expansion valves 114a and 114b are adjusted to the "Expansion" position, the inert gas is routed from the sample outlet port 118 to the inlet end 132 of the expansion chamber 128 via the conduit segment 136. The inert gas is pushed through the expansion chamber 128 to purge the body 130. Further, during purging operations, the pressure relief valve 140 is operated via the override device to an opened position, allowing the inert gas and any sample fluid purged from the expansion chamber 128 to exit the sampling device 100 via the fluid source inlet 120. Once the fluid sampling device has been sufficiently purged of residual sample fluid, the expansion chamber 128 can be restored to vacuum pressure using the vacuum port 137 coupled to the inlet end 132 of the chamber 128.

Figure 2:
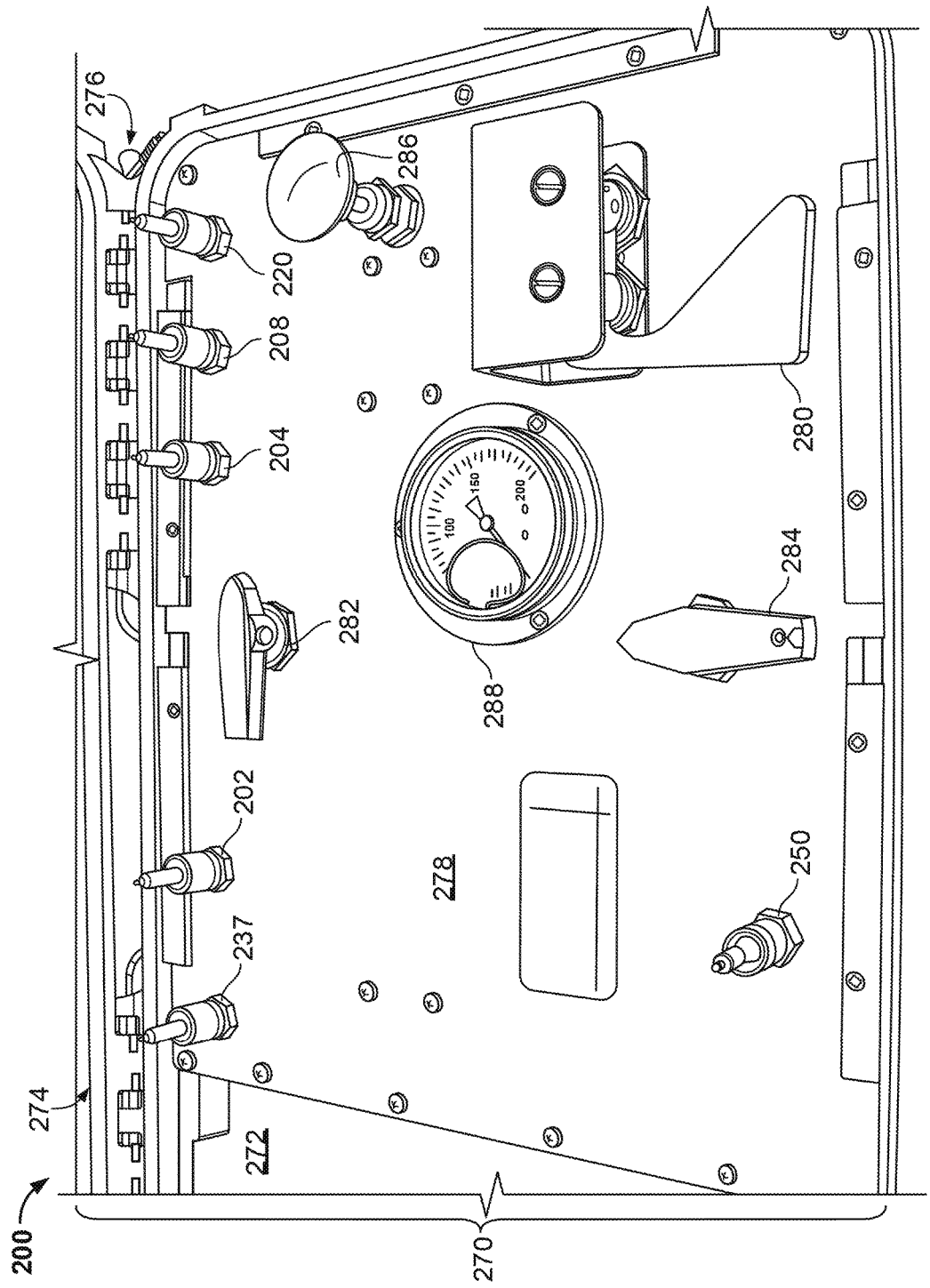
FIG. 2 is a perspective view of a portable fluid sampling device.
Figure 3:
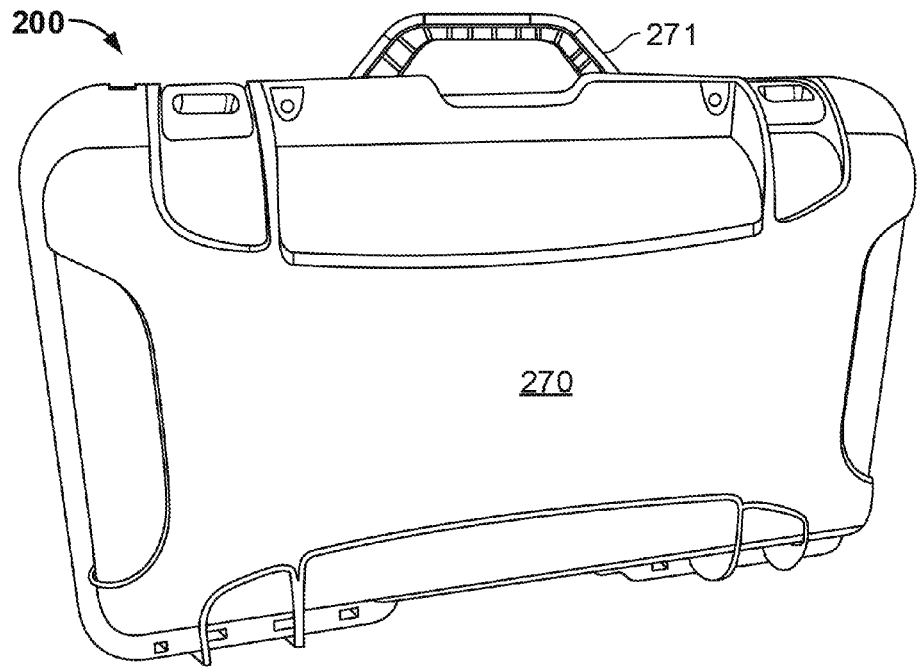
FIG. 3 is a side view of the portable fluid sampling device of FIG. 2 being carried by a user.

FIG. 2 is a perspective view of a portable fluid sampling device 200. In this example, the portable fluid sampling device 200 includes a housing 270 supporting a configuration of components that are similar or related to those described above in connection with the sampling device 100 of FIG. 1. Thus, various components carried by the housing 270 and depicted in FIG. 2 may be described with reference to a corresponding structure from the sampling device 100. As shown in FIG. 3, the housing 270 is a portable structure that can be readily transported throughout a worksite by a user grasping a handle 271 and carrying the housing 270. Returning to FIG. 2, in this example, the housing 270 includes a clamshell structure featuring a base 272 hingedly attached to a cover 274. Together, the base 272 and the cover 274 define an interior cavity 276. In some examples, the cover 274 can be locked down to the base 272 to close the housing 270 (e.g., during transportation by the user, as shown in FIG. 3). A faceplate 278 is mounted to the base 272 of the housing 270. Some of the components described below as carried by the housing 270 are mounted on the faceplate 278, while other components may be located beneath the faceplate 278 in a recess of the housing's base 272.

As shown in FIG. 2, the faceplate 278 supports a fluid source outlet 202, a fluid source inlet 220, a sample inlet port 204 and a sample outlet port 208. The fluid source outlet 202 and the fluid source inlet 220 can be coupled to an appropriate source of sample fluid, which may or may not provide sufficient pressure to circulate the fluid through the fluid sampling device 200. As described above, fluid received at the fluid source outlet 202 can be circulated to a sample vessel (e.g., the sample vessel 20) coupled to the sample inlet port 204 and outlet port 208 via one or more fluid conduit segments located beneath the faceplate 278. The faceplate 278 further supports an inert gas inlet 250, which can be coupled to a pressured source of inert gas (e.g., the inert gas source 30) for purging the fluid sampling device 200 and/or for driving a booster pump (e.g., booster pump 156) configured to increase the pressure of the sample fluid from the fluid source (e.g., the fluid source 10). The faceplate 278 further supports a vacuum port 237 coupled to the inlet end of an expansion chamber (e.g., the expansion chamber 128) located beneath the faceplate 278. As described above, the expansion chamber can be restored to vacuum pressure using the vacuum port 237 once the fluid sampling device has been sufficiently purged of residual sample fluid. In some embodiments, an external 1,000 cc cylinder that has been prepped to a vacuum pressure of about −200 psig can be coupled to the vacuum port 237 to restore vacuum pressure to the expansion chamber.

The faceplate 278 still further includes a four valve-actuator handles 280, 282, 284 and 286. The first valve-actuator handle 280 is installed to operate an expansion valve assembly (e.g., the valve assembly 114) configured to govern the flow of fluid between the external sample source, the external sample vessel, and the expansion chamber. The valve-actuator handle 282 is installed to operate a booster-pump valve (e.g., booster pump valve 110) configured to regulate the flow sample fluid to a suction port of the booster pump located beneath the faceplate 278. The valve-actuator handle 284 is installed to operate a gas routing valve (e.g., gas routing valve 152) configured to govern the flow inert gas between the intake port and the suction port of the booster pump located beneath the faceplate 278. The valve-actuator handle 286 is installed to operate a pressure relief valve (e.g., pressure relief valve 140) that is configured to automatically purge the expansion chamber located beneath the faceplate 278 when a predetermined activation pressure is reached. Accordingly, in this example, the valve-actuator handle 286 serves as a manual override device for opening and closing the pressure relief valve, for example, to facilitate on-demand purging of sample fluid from the expansion chamber with inert gas as described below in accordance with process 600 of FIG. 6. A pressure indicator 288 is installed to provide a pressure reading of the fluid circulating through the sampling device 200. Thus, for example, during a sampling process, a user can determine whether to engage the internal booster pump to inhibit or prevent flashing of the sample fluid.

Figure 4:
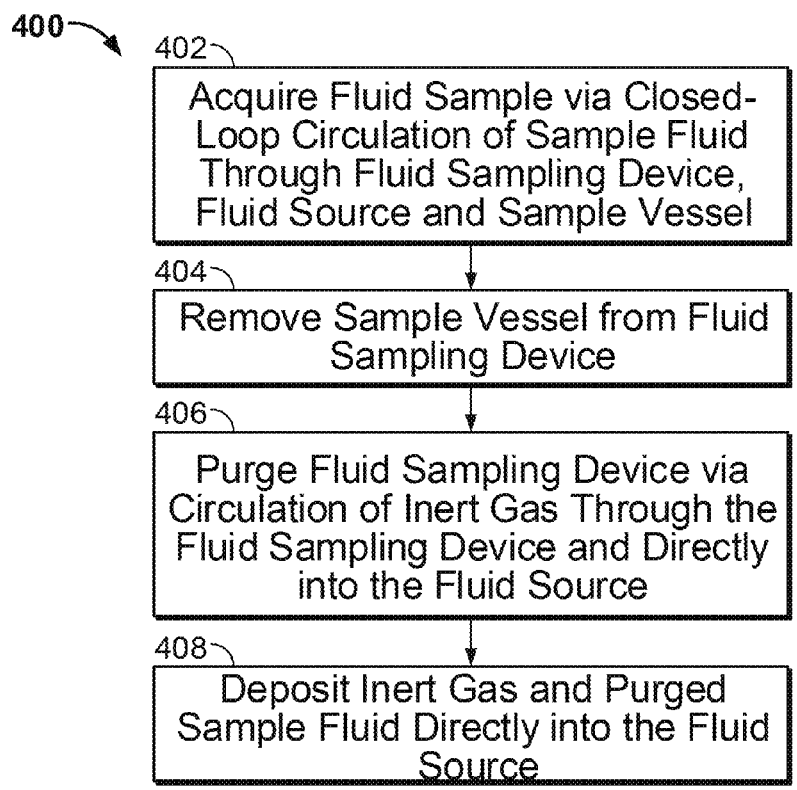
FIG. 4 is a flow chart illustrating a process of operating a fluid sampling device.
Figure 5:
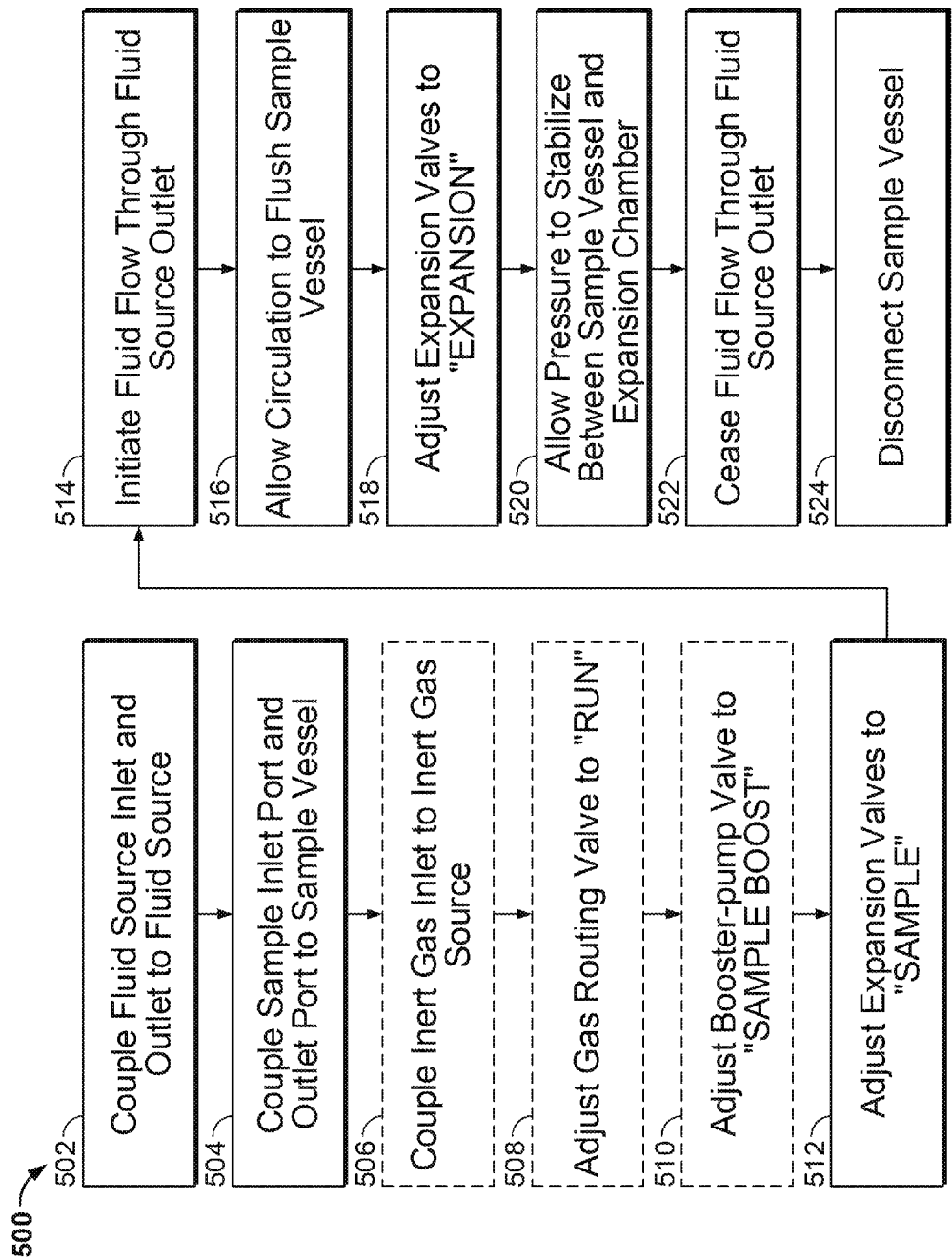
FIG. 5 is a flow chart illustrating a process of acquiring a fluid sample using a fluid sampling device.
Figure 6:
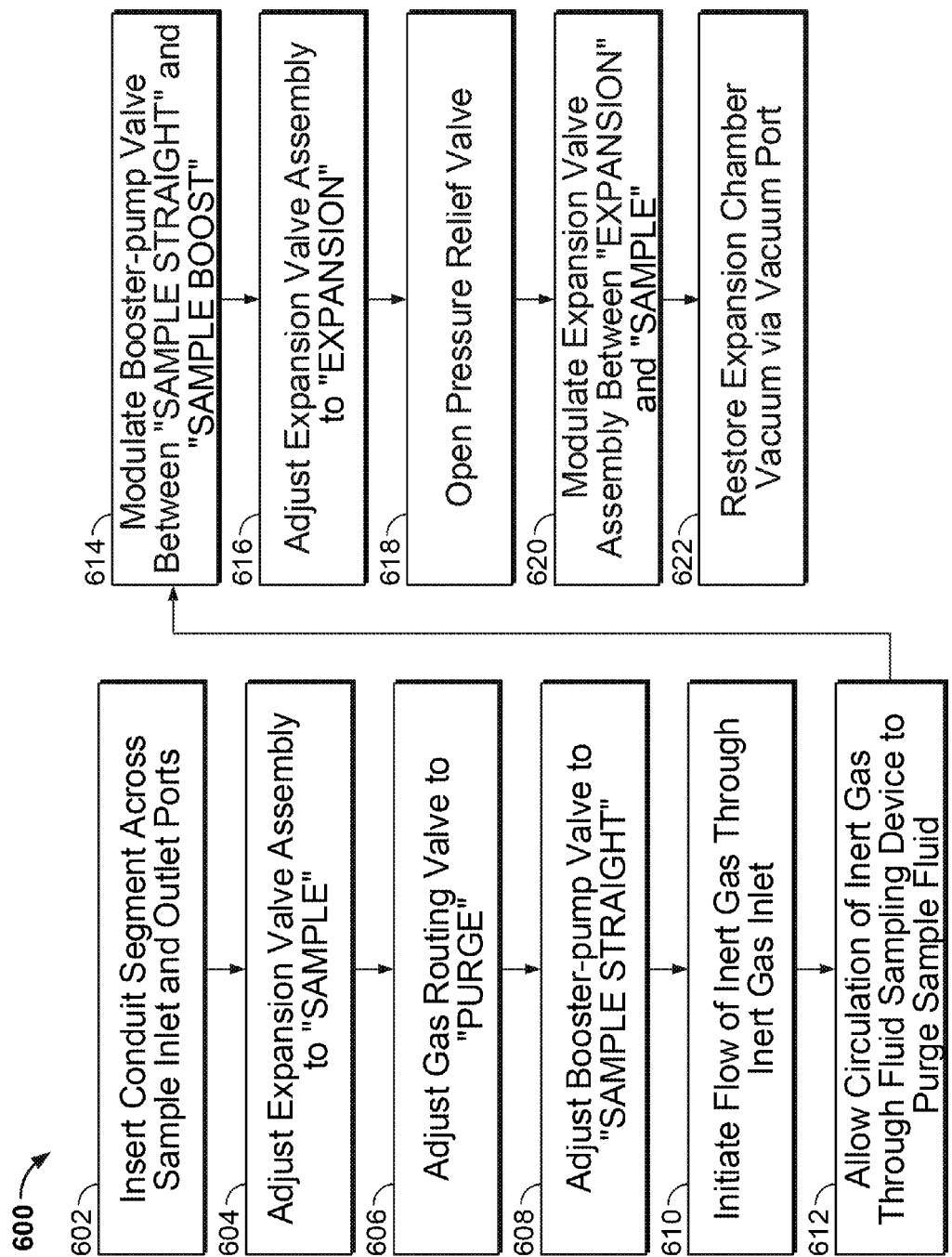
FIG. 6 is a flow chart illustrating a process of purging a fluid sampling device with inert gas.

FIG. 4 is a flow chart illustrating a process 400 of operating a fluid sampling device. FIG. 5 is a flow chart illustrating a process 500 of acquiring a fluid sample using a fluid sampling device. FIG. 6 is a flow chart illustrating a process 600 of purging a fluid sampling device with inert gas. The processes 400, 500 and 600 can be implemented, for example, in connection with one or more components of the fluid sampling device 100 shown in FIG. 1 and/or the portable fluid sampling device 200 shown in FIG. 2. Further, the operations of the processes do not require the any particular order to achieve desirable results. In addition, other operations may be provided, or operations may be eliminated, from the described processes without departing from the scope of the present disclosure.

According to the process 400 of FIG. 4, a fluid sample is acquired (402) via closed-loop circulation of sample fluid through a fluid sampling device, a fluid source and a sample vessel. As described above, the fluid sampling device may include one or more fluid conduits, valves, and chambers for facilitating the circulation of sample from the fluid source to the sample vessel. The fluid source may include a processing system for treating fluids (e.g., hydrocarbon fluids), a tank for storing the fluid, and/or any other suitable device or apparatus for containing or transporting fluid. The sample fluid may include liquefied petroleum gas, liquefied natural gas, or any other circulable fluid (e.g., compressed gas). The sample vessel and the expansion chamber may include any size or type of pressure vessel suitable for containing the sample fluid. In some implementations, the sample vessel may include a metallic, pressure-rated cylinder equipped with inlet and outlet isolation valves. Once the sample is acquired (402), the sample vessel is removed (404) from the fluid sampling device. After the sample vessel is removed (404), the fluid sampling device is purged (406) via circulation of inert gas through the fluid sampling device. The inert gas may include any gas-phase fluid that does not react with the sample fluid (e.g., compressed air, carbon dioxide, nitrogen gas, and oxygen gas). Circulated inert gas and purged sample fluid is deposited (408) directly into the fluid source. For example, as described above, the inert gas and sample fluid can be circulated throughout the various components of the fluid sampling device for purging and then directed through a fluid source inlet coupled to the fluid source.

According to the process 500 of FIG. 5, the fluid source inlet and the fluid source outlet of a fluid sampling device in accordance with one or more embodiments of the present disclosure is coupled (502) to a suitable fluid source. The sample inlet port and the sample outlet port of the fluid sampling device are coupled (504) to a suitable sample vessel. Optionally, an internal booster pump may be operated to maintain the sample fluid at a suitable pressure. To engage the booster pump, the inert gas inlet of the fluid sampling device is coupled (506) to an inert gas source; the gas routing valve is adjusted (508) to the "Run" position; and the booster-pump valve is adjusted (510) to the "Sample Boost" position. Alternatively, to bypass the booster pump, the gas routing valve can be adjusted to an "Off" position, the booster-pump valve can be adjusted to the "Sample Straight" position, and/or the inert gas source can be decoupled from the inert gas inlet. Regardless of the state of the booster pump, the expansion valve assembly is adjusted (512) to the "Sample" position. The flow of sample fluid through the fluid source outlet is initiated (514), and the flow of sample fluid is allowed to circulate (516) through the fluid sampling device to flush the sample vessel. As described above, in some examples, the fluid sampling device is configured to facilitate the closed-loop circulation of sample fluid between the sample vessel and the fluid source. Once the sample vessel has been flushed, the expansion valve assembly is adjusted (518) to the "Expansion" position, and the pressure between the sample vessel and the internal expansion chamber is allowed to stabilize (520). As described above, in some examples, the expansion chamber is maintained at a relatively low pressure compared to the sample vessel (e.g., a vacuum pressure), such that the pressure differential causes a portion of the fluid to vacate the sample vessel in favor of the expansion chamber. In some implementations, where the sample fluid is a compressed gas, at least a portion of the fluid in the sample vessel may undergo as liquid-to-gas phase change as a result of the pressure stabilization. After the fluid sample has been expanded, fluid flow through the fluid source outlet is ceased (522), and the sample vessel is disconnected (524) from the fluid sampling device.

According to the process 600 of FIG. 6, a conduit segment is inserted (602) across the sample inlet and outlet ports of the fluid sampling device, replacing the disconnected sample vessel. The expansion valve assembly is adjusted (604) to the "Sample" position, providing a continuous flow path between the fluid source outlet and inlet across the inserted conduit segment. The gas routing valve is adjusted (606) is adjusted to the "Purge" position. The booster-pump valve is adjusted (608) to the "Sample Straight" position. A flow of inert gas is initiated (610) through the inert gas inlet, and allowed to circulate (612) through the fluid sampling device to purge its components of residual fluid from the sampling process (e.g., the sampling process 500 of FIG. 5). The booster-pump valve is modulated (614) between the "Sample Straight" and "Sample Boost" positions. As described above, when the booster-pump valve is in the "Sample Boost" position, inert gas is pushed back through the booster-pump valve and the fluid source outlet. Thus, in some examples, modulating the booster-pump valve back and forth can cause discrete "puffs" or "jets" of inert gas to purge those components of sample fluid, which may be bypassed when the booster-pump valve is held in the "Sample Straight" position. Returning to FIG. 6, the expansion valve assembly is adjusted (616) to the "Expansion" position, exposing the inlet end of the expansion chamber to the inert gas flow. The pressure relief valve is opened (618), exposing the outlet end of the expansion chamber to the fluid source inlet. The expansion valve assembly is modulated (620) between the "Expansion" and "Sample" positions, to cause discrete "puffs" or "jets" of inert gas to purge the expansion chamber. Inert gas and residual sample fluid purged from the expansion chamber flow directly to the fluid source via the fluid source inlet. Once the fluid sampling device has been sufficiently purged of residual sample fluid, the expansion chamber is restored (622) to vacuum pressure using the vacuum port at the inlet end of the chamber.

A number of embodiments have been described. Nevertheless, it will be understood that various modifications may be made without departing from the spirit and scope of the inventions.

The invention claimed is:
1. A fluid sampling device comprising:
a first conduit configured to couple an outlet of a fluid source to a sample inlet port;
a second conduit configured to couple a sample outlet port to an inlet of the fluid source;
an expansion chamber comprising an inlet and an outlet coupled to the first and second conduits by a valve assembly; and
a pressure relief valve configured to couple the outlet of the expansion chamber to the inlet of the fluid source,
wherein the first conduit is further configured to be coupled to an inert gas source, such that:
inert gas from the inert gas source pushes fluid within the first and second conduits toward the inlet of the fluid source when the valve assembly is in a first position, thereby purging the first and second conduits, and
inert gas from the inert gas source pushes fluid within the expansion chamber towards the inlet of the fluid source when the valve assembly is in a second position and the pressure relief valve is opened, thereby purging the expansion chamber, and
wherein the valve assembly comprises a tandem valve including a pair of three-way valves, a first of the three-way valves coupling the inlet of the expansion chamber to the second conduit, and a second of the three-way valves coupling the outlet of the expansion chamber to first conduit.
2. The fluid sampling device of claim 1, further comprising a portable housing supporting the first and second conduits, the expansion chamber and the pressure relief valve.
3. The fluid sampling device of claim 1, further comprising a booster pump configured to be coupled to the first conduit, wherein operation of the booster pump induces fluid from the outlet of the fluid source to flow through the first conduit towards the sample inlet port.
4. The fluid sampling device of claim 3, wherein the booster pump comprises a gas drive, and wherein an intake port of the gas drive is configured to be coupled to the inert gas source.
5. The fluid sampling device of claim 4, further comprising an inert-gas routing valve configured to modulate coupling of the inert gas source between the first conduit and the intake port of the gas drive of the booster pump.

6. The fluid sampling device of claim 3, further comprising a booster-pump valve configured to modulate coupling of the first conduit with a high-pressure outlet of the booster pump.

7. A fluid sampling device comprising:
a first conduit configured to couple an outlet of a fluid source to a sample inlet port;
a second conduit configured to couple a sample outlet port to an inlet of the fluid source;
an expansion chamber comprising an inlet and an outlet coupled to the first and second conduits by a valve assembly;
a booster pump configured to be coupled to the first conduit, such that operation of the booster pump induces fluid from the outlet of the fluid source to flow through the first conduit towards the sample inlet port; and
a portable housing supporting the first and second conduits, the expansion chamber and the booster pump,
wherein the booster pump comprises a gas drive, and wherein an intake port of the gas drive is configured to be coupled to an inert gas source, and further comprising an inert-gas routing valve configured to modulate coupling of the inert gas source between the first conduit and the intake port of the gas drive of the booster pump.

8. The fluid sampling device of claim 7, further comprising a sample vessel coupled to the sample inlet port and the sample outlet port.

9. The fluid sampling device of claim 8, wherein fluid from the fluid source flows in a closed loop between the sample vessel and the fluid source when the valve assembly is in a first position, thereby flushing the sample vessel, and wherein the fluid flows in a closed loop between the sample vessel and the expansion chamber when the valve assembly is in a second position, thereby expanding a portion of the fluid in the sample vessel.

10. The fluid sampling device of claim 7, further comprising a booster-pump valve configured to modulate coupling of the first conduit with a high-pressure outlet of the booster pump.

11. A method of purging a fluid sampling device, the method comprising:
coupling a fluid conduit of the fluid sampling device to an inert gas source;
circulating the inert gas through the fluid conduit;
circulating the inert gas through an expansion chamber of the fluid sampling device;
circulating the inert gas through a valve assembly comprising a tandem valve including a pair of three-way valves, a first of the three-way valves coupling an inlet of the expansion chamber to the fluid conduit, and a second of the three-way valves coupling an outlet of the expansion chamber to the fluid conduit; and
depositing at least a portion of the inert gas and at least a portion of any sample fluid purged from the fluid conduit and the expansion chamber directly from the fluid sampling device to a source of the sample fluid coupled to the fluid sampling device.

12. The method of claim 11, further comprising:
modulating the valve assembly between first and second positions to cause discrete portions of inert gas to circulate through the expansion chamber.

13. The method of claim 11, further comprising:
engaging an override device of a pressure relief valve coupled to the outlet of the expansion chamber, thereby fluidically coupling the expansion chamber with the source of the sample fluid.

14. A fluid sampling device comprising:
a first conduit configured to couple an outlet of a fluid source to a sample inlet port;
a second conduit configured to couple a sample outlet port to an inlet of the fluid source;
an expansion chamber comprising an inlet and an outlet coupled to the first and second conduits by a valve assembly;
a pressure relief valve configured to couple the outlet of the expansion chamber to the inlet of the fluid source;
and a booster pump configured to be coupled to the first conduit, wherein operation of the booster pump induces fluid from the outlet of the fluid source to flow through the first conduit towards the sample inlet port, and wherein the booster pump comprises a gas drive, and wherein an intake port of the gas drive is configured to be coupled to an inert gas source, and
wherein the first conduit is further configured to be coupled to the inert gas source, such that:
inert gas from the inert gas source pushes fluid within the first and second conduits toward the inlet of the fluid source when the valve assembly is in a first position, thereby purging the first and second conduits, and
inert gas from the inert gas source pushes fluid within the expansion chamber towards the inlet of the fluid source when the valve assembly is in a second position and the pressure relief valve is opened, thereby purging the expansion chamber.

15. The fluid sampling device of claim 14, further comprising a portable housing supporting the first and second conduits, the expansion chamber, and the pressure relief valve.

16. The fluid sampling device of claim 14, further comprising an inert-gas routing valve configured to modulate coupling of the inert gas source between the first conduit and the intake port of the gas drive of the booster pump.

17. The fluid sampling device of claim 14, further comprising a booster-pump valve configured to modulate coupling of the first conduit with a high-pressure outlet of the booster pump.

18. A fluid sampling device comprising:
a first conduit configured to couple an outlet of a fluid source to a sample inlet port;
a second conduit configured to couple a sample outlet port to an inlet of the fluid source;
an expansion chamber comprising an inlet and an outlet coupled to the first and second conduits by a valve assembly;
a booster pump configured to be coupled to the first conduit, such that operation of the booster pump induces fluid from the outlet of the fluid source to flow through the first conduit towards the sample inlet port; and
a portable housing supporting the first and second conduits, the expansion chamber, and the booster pump,
wherein the valve assembly comprises a tandem valve including a pair of three-way valves, a first of the three-way valves coupling the inlet of the expansion chamber to the second conduit, and a second of the three-way valves coupling the outlet of the expansion chamber to first conduit.

19. The fluid sampling device of claim 18, further comprising a sample vessel coupled to the sample inlet port and the sample outlet port.

20. The fluid sampling device of claim 19, wherein fluid from the fluid source flows in a closed loop between the sample vessel and the fluid source when the valve assembly is in a first position, thereby flushing the sample vessel, and wherein the fluid flows in a closed loop between the sample vessel and the expansion chamber when the valve assembly is in a second position, thereby expanding a portion of the fluid in the sample vessel.

21. The fluid sampling device of claim 18, further comprising a booster-pump valve configured to modulate coupling of the first conduit with a high-pressure outlet of the booster pump.

\* \* \* \* \*